United States Patent [19]

Miyahara et al.

[11] Patent Number: 5,102,525

[45] Date of Patent: Apr. 7, 1992

[54] PLANAR OXYGEN SENSOR

[75] Inventors: Yuji Miyahara, Hitachi; Keiji Tsukada, Katsuta; Yasuhisa Shibata, Ibaraki; Hiroyuki Miyagi, Kokubunji, all of Japan

[73] Assignee: Hitachi, Ltd., Tokyo, Japan

[21] Appl. No.: 625,014

[22] Filed: Dec. 10, 1990

[30] Foreign Application Priority Data

Dec. 14, 1989 [JP] Japan .................. 1-324227

[51] Int. Cl.[5] .............................. G01N 26/27
[52] U.S. Cl. ......................... 204/415; 204/412; 204/426; 204/414
[58] Field of Search ............... 204/128, 412, 426, 415, 204/414

[56] References Cited

U.S. PATENT DOCUMENTS

| H. 427 | 2/1988 | Hirale et al. | 204/426 |
|---|---|---|---|
| 4,076,596 | 2/1978 | Connery et al. | 204/415 |
| 4,277,323 | 7/1981 | Muller et al. | 204/426 |
| 4,304,652 | 12/1981 | Chiba et al. | 204/426 |
| 4,439,911 | 4/1984 | Ikezawa et al. | 204/426 |
| 4,462,890 | 7/1984 | Touda et al. | 204/426 |
| 4,587,105 | 5/1986 | Bonne et al. | 204/426 |
| 4,668,374 | 5/1987 | Bhagat et al. | 204/426 |
| 4,724,061 | 2/1988 | Nyberg | 204/426 |
| 4,734,170 | 3/1988 | Oda et al. | 204/128 |
| 4,795,542 | 1/1989 | Ross et al. | 204/415 |
| 4,874,500 | 10/1989 | Madou et al. | 204/412 |
| 4,908,118 | 3/1990 | Ammende et al. | 204/426 |
| 4,913,792 | 4/1990 | Nagata et al. | 204/426 |
| 4,931,168 | 6/1990 | Watanabe et al. | 204/426 |

Primary Examiner—John Niebling
Assistant Examiner—Bruce Bell
Attorney, Agent, or Firm—Fay, Sharpe, Beall, Fagan, Minnich & McKee

[57] ABSTRACT

A planar oxygen sensor has an insulating substrate, a cathode formed on the insulating substrate generally at the center thereof; another electrode formed on the insulating substrate in a region other than the region of the cathode, a gas permeable membrane stretched to cover these electrodes and having its peripheral portion supported on the insulating substrate, and an electrolytic solution charged between the gas permeable membrane and the insulating substrate. A surface of the cathode is substantially in contact with the gas permeable membrane and is formed at a position higher than the gas permeable membrane support portion of the insulating substrate. A portion of the insulating substrate surface other than the region where the cathode is formed is recessed. Because the layer of electrolytic solution on the cathode is thin, oxygen molecules passing through the gas permeable membrane can immediately serve for the reduction at the cathode, thereby increasing the response speed of the planar oxygen sensor. Also, the amount of electrolytic solution is increased by the recess to extend the life of the sensor.

33 Claims, 5 Drawing Sheets

PLANAR OXYGEN SENSOR

BACKGROUND OF THE INVENTION

1. Field of the Invention

The present invention relates generally to oxygen sensors and, more particularly, to a planar oxygen sensor.

2. Description of the Related Art

A type of planar oxygen sensor such as the one described on pages 249 to 258 of "Sensors and Actuators 9" (1986) is known.

That is, this planar oxygen sensor has a sensor portion fabricated on a $SiO_2$ film formed on a silicon substrate. This sensor portion includes a polyimide frame formed to surround a region of the $SiO_2$ film, a cathode formed directly on the $SiO_2$ film generally at the center of the frame, an anode formed directly on the $SiO_2$ film between the frame and the cathode, an electrolytic solution which fills the interior of the frame and in which the anode is immersed, and a gas permeable membrane which covers the internal electrolytic solution and which is supported by the frame.

This planar oxygen sensor has an anode. However, a three-electrode planar oxygen sensor is known which has a reference electrode and a counter electrode instead of an anode.

In the conventional planar oxygen sensors, as described above, a gap is formed between the gas permeable membrane and the cathode, and a comparatively large amount of electrolytic solution exists in this gap. The following problem is therefore encountered. When a partial pressure of oxygen in the atmosphere changes, oxygen molecules are diffused in the large amount of electrolytic solution through the gas permeable membrane, so that the time taken by oxygen molecules to reach the surface of the cathode and to cause a current change by the reduction on the cathode is comparatively long.

The oxygen sensor having two electrodes, i.e., a cathode and an anode entail the problem of the anode being dissipated as a current flows by the reduction of oxygen. If, for example, the cathode is formed of platinum while the anode is formed of silver and silver chloride, the dissipation of the anode are expressed by the following chemical formulae:

Cathode $O_2 + 2H_2O + 4e^- \rightarrow 4OH^-$

Anode $4Ag + 4Cl^- \rightarrow 4AgCl + 4e^-$

As is apparent from these formulae, at the anode an irreversible reaction takes place for a change from silver to silver chloride. Ordinarily, the durability of oxygen sensors depends upon the amount of anode material. For this reason, the life of the oxygen sensor is short if the size of the sensor is reduced. Also, in small-size oxygen sensors, a composition change due to evaporation of water in the electrolyte causes a drift of the output current from the oxygen sensor.

SUMMARY OF THE INVENTION

The present invention has been achieved in consideration of these circumstances, and an object of the present invention is to provide a planar oxygen sensor having a high response speed as well as a long life.

To achieve this object, according to the present invention, there is provided a planar oxygen sensor basically having: an insulating substrate: a frame formed so as to surround at least a part of a major surface of the insulating substrate; a cathode formed on the insulating substrate generally at the center of the frame; another electrode formed on the insulating substrate between the frame and the cathode; a gas permeable membrane stretched to cover the cathode and the other electrode and having its peripheral portion supported on the frame; and an electrolytic solution charged between the gas permeable membrane, the frame and the insulating substrate; wherein a surface of the cathode is substantially in contact with the gas permeable membrane and is positioned higher than the gas permeable membrane support portion of the frame. A portion of the insulating substrate surface inside the gas permeable membrane support portion other than the region where the cathode is formed is recessed.

According to the present invention, there is also provided a planar oxygen sensor having: an insulating substrate; a cathode formed on the insulating substrate generally at the center thereof; another electrode formed in a region of the insulating substrate other than the region where the cathode is formed; a gas permeable membrane stretched to cover the cathode and the other electrode and having its peripheral portion supported on the insulating substrate; and an electrolytic solution charged between the gas permeable membrane and the insulating substrate; wherein a surface of the cathode is substantially in contact with the gas permeable membrane and is positioned higher than the gas permeable membrane support portion of the insulating substrate.

According to the present invention, there is further provided a planar oxygen sensor having: an insulating substrate; a frame formed so as to surround at least a part of a major surface of the insulating substrate; a working electrode formed on the insulating substrate generally at the center of the frame; a counter electrode and reference electrode formed on the insulating substrate between the frame and the working electrode; a gas permeable membrane stretched to cover the working electrode, the counter electrode and the reference electrode and having its peripheral portion supported on the frame; and an electrolytic solution charged between the gas permeable membrane, the frame and the insulating substrate; wherein a surface of the working electrode is substantially in contact with the gas permeable membrane and is positioned higher than the gas permeable membrane support portion of the frame.

According to the present invention, as described above, the surface of the cathode or the working electrode is substantially in contact with the gas permeable membrane. The gas permeable membrane can be brought into contact with the cathode substantially positively because the position of the gas permeable membrane support portion is lower than that of the surface of the cathode. The amount of electrolytic solution forming a layer between the cathode and the gas permeable membrane is therefore very small and oxygen molecules diffused through the gas permeable membrane can be speedily diffused in the electrolyte layer and can immediately serve for the reduction at the cathode. The response speed of the oxygen sensor can therefore be greatly increased.

If a three-electrode structure is adopted, the working electrode and the counter electrode may be formed of platinum having a high corrosion resistance to prevent dissipation of these electrodes caused by the reduction current flowing between these electrodes. It is thereby possible to obtain the output current with stability during long-time use.

Because a region of the insulating substrate surface inside the gas-permeable support portion other than the region where the cathode or the working electrode is formed is recessed, the amount of charged electrolytic solution can be increased and any abrupt change in the composition of the electrolytic solution due to evaporation can be prevented. It is thereby possible to reduce the drift of the output current caused by a change in the electrolyte composition.

DETAILED DESCRIPTION OF THE PREFERRED EMBODIMENTS

Figure 1:
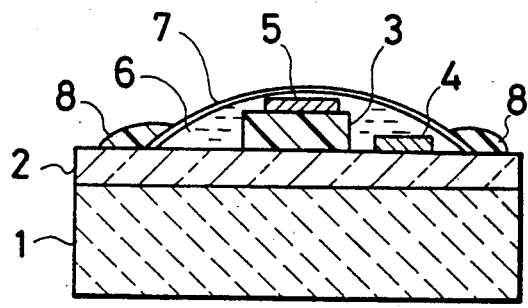
FIG. 1 is a cross-sectional view of the construction of a planar oxygen sensor which represents an embodiment of the present invention.

FIG. 1 shows in section a planar oxygen sensor in accordance with the first embodiment of the present invention. A $SiO_2$ film 2 is formed on a major surface of a silicon substrate 1. A support pad 3 formed of, for example, polyimide is formed on the surface of the $SiO_2$ film 2 generally at the center thereof, and a cathode 5 is formed on an upper surface of the support pad 3. Each of the support pad 3 and the cathode 5 can be formed by the well-known photolithography technique. Platinum, for example, is used as the material of the cathode 5. To improve adhesion between the support pad 3 and the cathode 5, a metallic layer may be interposed therebetween. If the support pad 3 and the cathode 5 are formed of the above materials, then Ti, Cr, Cu or the like can be selected as the material of the metallic layer. An anode 4 is formed in a part of the region of the $SiO_2$ film 2 other than the region where the support pad 3 is formed. The anode 4 can also be formed by the photolithography technique. For example, the anode 4 is formed of silver (Ag)/silver chloride (AgCl). Needless to say, a metallic layer may be interposed between the anode 4 and the $SiO_2$ film 2 to improve the adhesion therebetween. A gas permeable membrane 7 which covers the support pad 3, the cathode 5 and the anode 4 is formed above the $SiO_2$ film 2 on which the support pad 3, the cathode 5 and the anode 4 are formed. A peripheral portion of the gas permeable membrane 7 is supported on the $SiO_2$ film 2. The peripheral portion of the gas permeable membrane 7 is fixed to the $SiO_2$ film 2 by an adhesive 8 which is, for example, an epoxy resin. The space defined between the gas permeable membrane 7 and the $SiO_2$ film 2 is filled with an electrolytic solution 6. The electrolytic solution 6 may be replaced with an electrolytic gel.

In the planar oxygen sensor thus constructed, the gas permeable membrane 7 support portion is positioned lower than the surface of the cathode 5, so that the surface of the cathode 5 is substantially in contact with the gas permeable membrane 7. The amount of electrolytic solution 6 between the cathode 5 and the gas permeable membrane 7 is therefore very small and oxygen molecules diffused from the gas permeable membrane 7 can immediately serve for the reduction at the cathode 5. It is thereby possible to greatly increase the response speed of the oxygen sensor.

Figure 2:
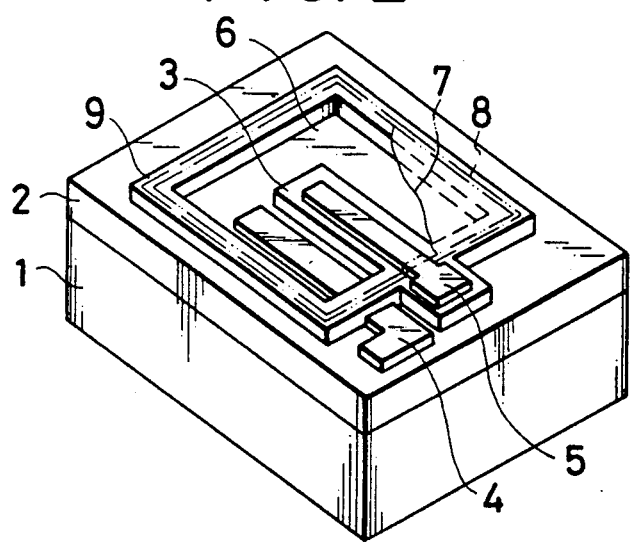
FIG. 2 is a perspective view of a planar oxygen sensor which represents a second embodiment of the present invention.

FIG. 2 shows in perspective the construction of a planar oxygen sensor in accordance with the second embodiment of the present invention. In FIG. 2, members identical or corresponding to those shown in FIG. 1 are indicated by the same reference characters. The construction of this planar oxygen sensor differs from that shown in FIG. 1 in that a peripheral portion of the gas permeable membrane 7 is supported on an upper surface of a frame 9 formed on the $SiO_2$ film 2. The frame 9 is formed of, for example, polyimide, and the gas permeable membrane 7 is bonded by, for example, an epoxy resin. In this case, the bonded gas permeable membrane 7 support portion is also positioned lower than the surface of the cathode 5 as in the case of the arrangement shown in FIG. 1.

Figure 3:
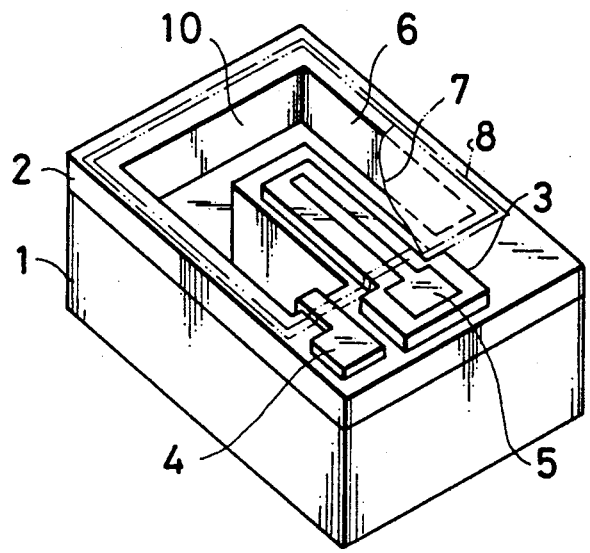
FIG. 3 is a perspective view of a planar oxygen sensor which represents a third embodiment of the present invention.

FIG. 3 shows in perspective the construction of a planar oxygen sensor in accordance with the third embodiment of the present invention. In FIG. 3, members identical or corresponding to those shown in FIG. 1 are indicated by the same reference characters. The construction of this planar oxygen sensor differs from that shown in FIG. 1 in that a recess 10 is formed in a part of the region of the $SiO_2$ film 2 inside the gas permeable membrane 7 support portion other than the region where the support pad 3 is formed. This recess 10 is formed by recessing the silicon substrate 1. The $SiO_2$ film 2 is formed on side and bottom surfaces of the recess of the substrate 1, and the anode 4 is formed on the $SiO_2$ film 2 on the recessed bottom.

In this construction, the recess 10 is also filled with the electrolytic solution 6 and the amount of electrolytic solution can therefore be increased. It is thereby possible to charge a predetermined amount of electrolytic solution 6 with improved reproducibility and, hence, to limit variations in the product characteristics when oxygen sensors are manufactured. It is also possible to limit the relative composition change caused when water in the electrolytic solution is evaporated.

Figure 4:
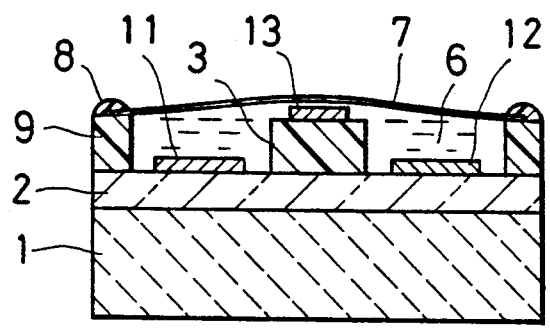
FIG. 4 is a cross-sectional view of a planar oxygen sensor which represents a fourth embodiment of the present invention.

FIG. 4 shows in section the construction of a planar oxygen sensor in accordance with the fourth embodiment of the present invention. In FIG. 4, members identical or corresponding to those shown in FIG. 1 are indicated by the same reference characters. First, the electrodes of this planar oxygen sensor are different from those shown in FIG. 1. That is, a working electrode 13 is formed on the upper surface of the support pad 3, and a counter electrode 11 and a reference electrode 12 are formed in a region of the upper surface of the $SiO_2$ film 2 other than the region where the support pad 3 is formed. A polyimide frame 9 is formed on the $SiO_2$ film 2 so as to surround the support pad 3, the counter electrode 11 and the reference electrode 12, as in the case of the arrangement shown in FIG. 3. A peripheral portion of the gas permeable membrane 7 is fixed to a portion of the frame 9 by an adhesive 8 which comprises an epoxy resin. The space surrounded by the gas permeable membrane 7, the $SiO_2$ film 2 and the frame 9 is filled with electrolytic solution 6 as in the case of the arrangement shown in FIG. 3.

Thus, a three-electrode structure is provided which includes the working electrode 13, the counter electrode 11 and the reference electrode 12. The working electrode 13 and the counter electrode 11 are formed of platinum (Pt). A constant voltage is applied to the working electrode 13 by the reference electrode 12 to make an oxygen reduction current flow between the counter electrode 11 and the working electrode 13. Dissipation of these electrodes caused by the reduction current flowing between the counter electrode 11 and the working electrode 13 is thereby prevented.

Figure 5:
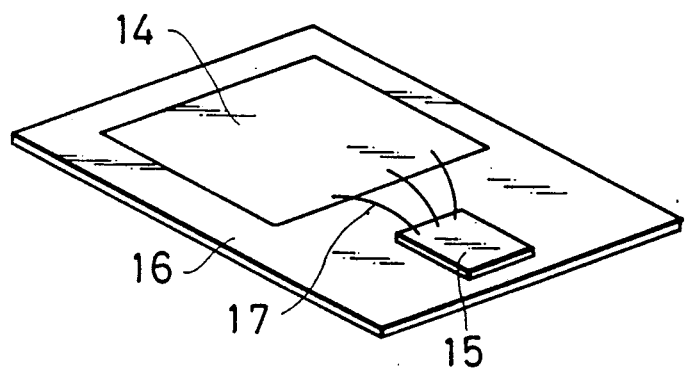
FIG. 5 is a perspective view of an example in which the planar oxygen sensor in accordance with the present invention is assembled on one substrate together with a potentiostat circuit.
Figure 6:
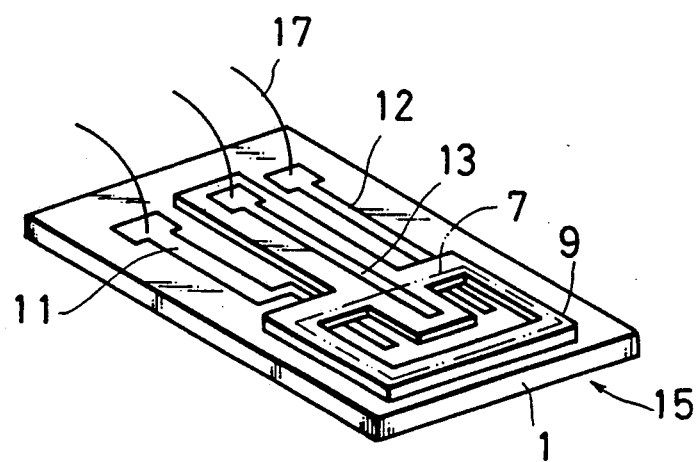
FIG. 6 is another perspective view of the embodiment shown in FIG. 5.
Figure 7:
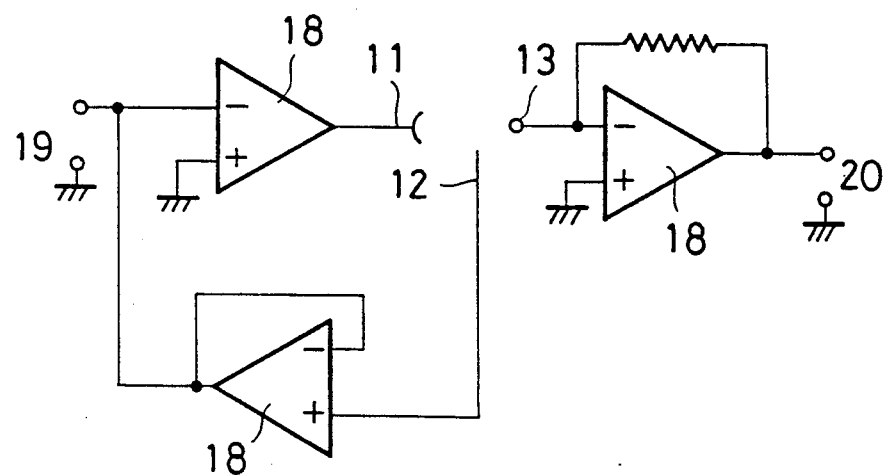
FIG. 7 is a circuit diagram of an example of the potentiostat circuit of FIG. 5.

FIG. 5 shows in perspective the construction of an example in which the above planar oxygen sensor is formed together with an external circuit on one printed circuit board. As shown in FIG. 5, a planar oxygen sensor 15 is mounted in a region of the surface of a printed circuit board 16, and a potentiostat circuit 14 is formed in another region of this circuit board surface. The planar oxygen sensor 15 has a three-electrode structure, such as that shown in FIG. 4, in which lead electrodes of the working electrode 13, the counter electrode 11 and the reference electrodes are formed on the same silicon substrate as shown in FIG. 6. These lead electrodes are connected to the potentiostat circuit 14 by bonding wires 17. The potentiostat circuit 14 is formed by three operational amplifiers 18 as shown in FIG. 7. A voltage of 0.8 V is applied to a terminal 19 shown in FIG. 7, and an output voltage is obtained from an oxygen reduction current flowing between the counter electrode 11 and the working electrode 13 and is output through a terminal 20.

Figure 8:
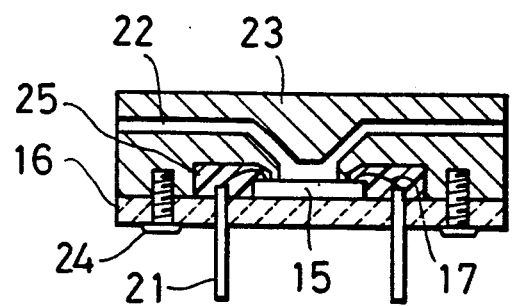
FIG. 8 is a cross-sectional view of an example of a flow cell incorporating the planar oxygen sensor in accordance with the present invention.

Next, the characteristics of the planar oxygen sensor shown in FIG. 2 will be described below. For this planar oxygen sensor, the thickness of the $SiO_2$ film 2 was set to 300 nm, and the thickness of the support pad 3 was set to 50 $\mu$m. The anode 4 was formed as a Ti/Ag/AgCl three-layer film, the cathode 5 was formed as a Ti/Pt two-layer film. An electrolytic gel was used as the electrolyte 6 in this case. More specifically, the electrolytic gel was prepared by dissolving polyvinyl alcohol in a mixture solution of a pH 6.86 phosphoric acid buffer solution and 10 mM KCl. A Teflon film ("Teflon" is the trademark for polytetrafluoroethylene) having a thickness of 12.5 $\mu$m was used as the gas permeable membrane 7. The planar oxygen sensor thus manufactured was set in a flow cell such as that shown in FIG. 8. This flow cell is constructed as described below. In the flow cell, the planar oxygen sensor 15 is die-bonded to a major surface of the printed circuit board 16, and the electrodes of the planar oxygen sensor 15 are connected to pins 21 by wires 17. The pins 21 are embedded in the printed circuit board 16 and are led to the reverse side of the printed circuit board 16. A cap 23 is formed on the major surface of the printed circuit board 16 where the planar oxygen sensor 15 is formed. The cap 23 is fixed on the printed circuit board 16 by screws 24. A flow passage 22 having a side surface defined by the gas permeable membrane 7 is formed in the flow cell. The electrodes, the wires 17 and the end of the pins 21 to which the wires 17 are connected are covered with an epoxy resin 25 to prevent contact between these elements and the specimen flowing in the flow passage 22.

Figure 9:
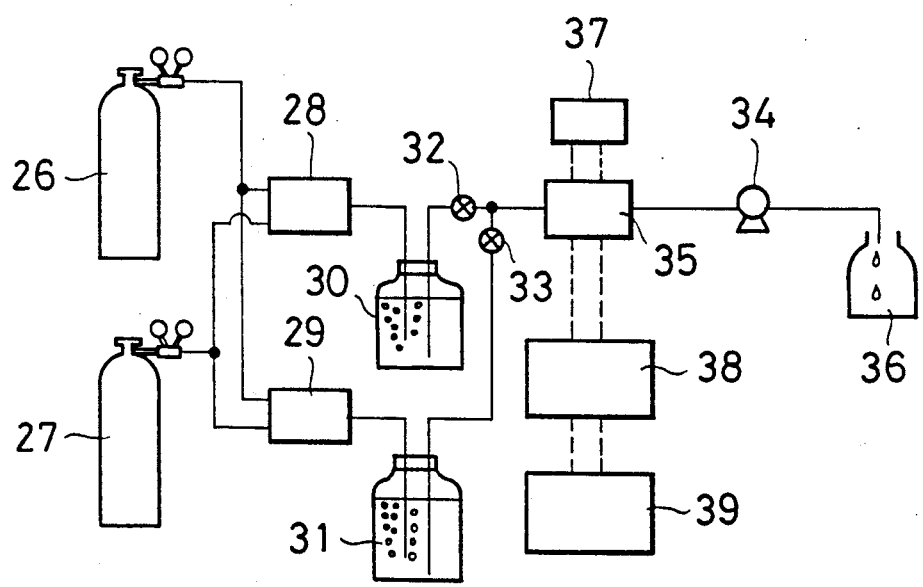
FIG. 9 is a diagram of an example of a measuring system including the flow cell shown in FIG. 8.

The thus-constructed flow cell was set in a measuring system such as that shown in FIG. 9. Referring to FIG. 9, a 100% oxygen gas bomb 26 and a 100% nitrogen gas bomb 27 are provided. The 100% oxygen gas and the 100% nitrogen gas are supplied from these gas bombs to gas mixers 28 and 29. A 20% oxygen gas and a 10% oxygen gas are respectively produced by the gas mixers 28 and 29. These gases are introduced into bubblers 30 and 31. The pH 6.86 phosphoric acid buffer solution is contained in the bubblers 30 and 31, and two amounts of dissolved oxygen of different concentrations are thereby prepared. These amounts of dissolved oxygen are alternately introduced into a flow cell 35 by opening/closing valves 32 and 33 and by operating a drawing pump 34. A voltage of $-0.7$ V is applied between the cathode and the anode by a power source 37, and a current flowing between the cathode and the anode is measured with an ammeter 38. The measured value is recorded by a recorder 39. The specimen solution after measurement in the flow cell 35 is collected in a bottle 36.

Figure 10:
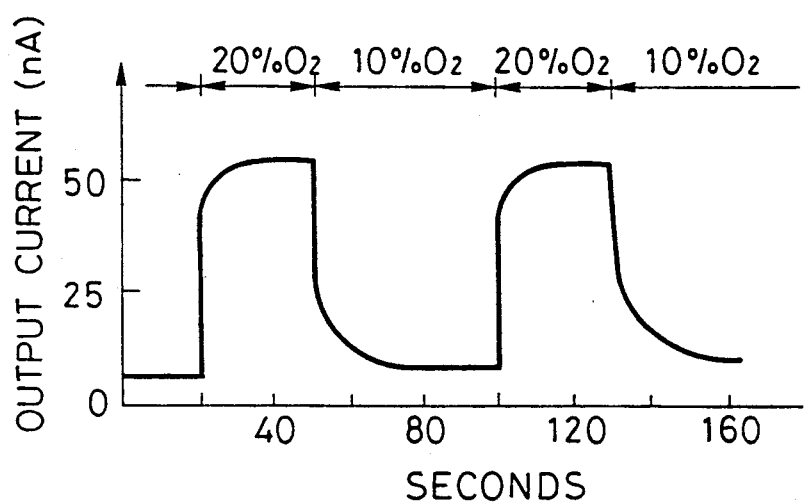
FIGS. 10 and 11 are graphs of the results of experiments showing the effects of the planar oxygen sensor in accordance with the present invention.

The results recorded by the recorder were as shown in FIG. 10 in which the output current in the case of each of the 20% oxygen gas and the 10% oxygen gas is shown with respect to time. The output current rises and falls at high rates. It is thereby understood that the oxygen sensor in accordance with the present invention is improved in response.

Figure 11:
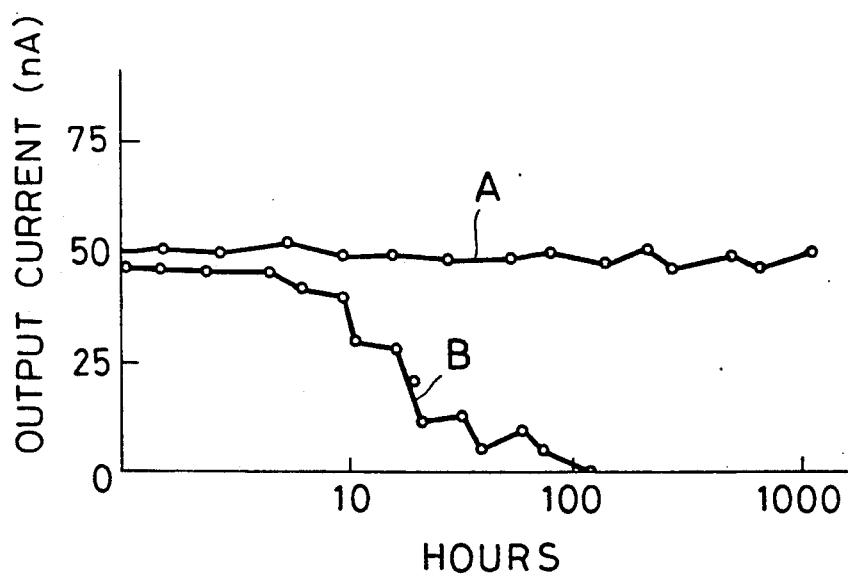

FIG. 11 is a graph of the output currents of a three-electrode structure sensor and a two-electrode structure sensor detected with respect to time. A curve A represents a characteristic of the three-electrode structure sensor while a curve B represents a characteristic of the two-electrode structure sensor. As is apparent from this graph, the three-electrode structure sensor can maintain the output current for a long time and has an extended life.

As is apparent from the foregoing, since in the planar oxygen sensor of the present invention the gas permeable membrane support portion is positioned lower than the surface of the cathode or the working electrode, the surface of the cathode or the working electrode is substantially in contact with the gas permeable membrane. The amount of electrolytic solution between the cathode or the working electrode and the gas permeable membrane is therefore very small and oxygen molecules diffused from the gas permeable membrane can immediately serve for the reduction at the cathode. It is thereby possible to greatly increase the response speed of the planar oxygen sensor.

If a three-electrode structure is adopted, the working electrode and the counter electrode may be formed of platinum having a high corrosion resistance to prevent dissipation of these electrodes caused by the reduction current flowing between these electrodes. It is thereby possible to maintain the output current with stability during long-time use.

Since a region of the insulating substrate surface inside the gas-permeable support portion other than the region where the cathode or the working electrode is formed is recessed, the amount of charged electrolytic solution can be increased and any abrupt change in the composition of the electrolytic solution due to evaporation can be prevented. It is thereby possible to reduce the drift of the output current caused by a change in the electrolyte composition.

What is claimed is:

1. A planar oxygen sensor comprising:
   an insulating substrate;
   a frame formed so as to surround at least a part of a major surface of said insulating substrate;
   a cathode formed on said insulating substrate generally at the center of the part of the major surface surrounded by said frame;
   an anode formed on said insulating substrate between said frame and said cathode;
   a gas permeable membrane stretched over a portion of said insulating substrate to define an electrolyte chamber therebetween, said gas permeable membrane thereby covering said cathode and said anode within the electrolyte chamber and having a peripheral portion supported on said frame; and
   an electrolytic solution in said electrolyte chamber defined between said gas permeable membrane, said frame and said insulating substrate;
   wherein the peripheral portion of the gas permeable membrane is supported on said frame at a locus of support points, one said support point being displaced a minimum distance from said insulating substrate greater than or equal to the minimum such displacement of all other said support points, and wherein said cathode has a surface that is displaced from said insulating substrate a distance greater than that of said one support point in the same direction as said one support point displacement, said direction being toward a non-peripheral portion of said stretched gas permeable membrane.

2. A planar oxygen sensor according to claim 1, wherein a portion of the insulating substrate surface inside the electrolyte chamber, other than the region where said cathode is formed, is formed as a recessed bottom surface with respect to the portion of the insulating substrate on which said cathode is formed.

3. A planar oxygen sensor according to claim 1, wherein said cathode is formed of platinum.

4. A planar oxygen sensor according to claim 1, wherein said insulating substrate comprises a silicon dioxide film.

5. A planar oxygen sensor comprising:
   an insulating substrate;
   a cathode formed on said insulating substrate generally at the center thereof;
   an anode formed in a region of said insulating substrate other than the region where said cathode is formed;
   a gas permeable membrane stretched over a portion of said insulating substrate to define an electrolyte chamber therebetween, said gas permeable membrane thereby covering said cathode and said anode within the electrolyte chamber and having a peripheral portion supported on said insulating substrate; and
   an electrolytic solution in said electrolyte chamber defined between said gas permeable membrane and said insulating substrate;
   wherein the peripheral portion of the gas permeable membrane is supported on said insulating substrate at a locus of support points, one said support point being displaced a minimum distance from said insulating substrate greater than or equal to the minimum such displacement of all other said support points, and wherein said cathode has a surface that is displaced from said insulating substrate a distance greater than that of said one support point in the same direction as said one support point displacement, said direction being toward a non-peripheral point of said stretched gas permeable membrane.

6. A planar oxygen sensor according to claim 5, wherein a portion of the insulating substrate surface inside the electrolyte chamber, other than the region where said cathode is formed, is formed as a recessed bottom surface with respect to the portion of the insulating substrate on which said cathode is formed.

7. A planar oxygen sensor according to claim 5, wherein said cathode is formed of platinum.

8. A planar oxygen sensor according to claim 5, wherein said insulating substrate comprises a silicon dioxide film.

9. A planar oxygen sensor comprising:
   an insulating substrate;
   a frame formed so as to surround at least a part of a major surface of said insulating substrate;
   a working electrode formed on said insulating substrate generally at the center of the part of the major surface surrounded by said frame;
   a counter electrode and a reference electrode formed on said insulating substrate between said frame and said working electrode;
   a gas permeable membrane stretched over a portion of said insulating substrate to define an electrolyte chamber therebetween, said gas permeable membrane thereby covering said working electrode, said counter electrode and said reference electrode within the electrolyte chamber and having a peripheral portion supported on said frame; and
   an electrolytic solution in said electrolyte chamber defined between said gas permeable membrane, said frame and said insulating substrate;
   wherein the peripheral portion of the gas permeable membrane is supported on said frame at a locus of support points, one said support point being displaced a minimum distance from said insulating substrate greater than or equal to the minimum such displacement of all other said support points, and wherein said working electrode has a surface that is displaced from said insulating substrate a distance greater than that of said one support point in the same direction as said one support point displacement, said direction being toward a non-peripheral portion of said stretched gas permeable membrane.

10. A planar oxygen sensor according to claim 9, wherein a portion of the insulating substrate surface inside the electrolyte chamber, other than the region where said working electrode is formed, is formed as a recessed bottom surface with respect to the portion of the insulating substrate on which said working electrode is formed.

11. A planar oxygen sensor according to claim 9, wherein said reference electrode serves to apply a constant voltage to said working electrode.

12. A planar oxygen sensor according to claim 9, wherein each of said working electrode and said counter electrode is formed of platinum.

13. A planar oxygen sensor according to claim 9, wherein said insulating substrate comprises a silicon dioxide film.

14. A planar oxygen sensor comprising:
an insulating substrate;
a working electrode formed on said insulating substrate generally at the center thereof;
a counter electrode and a reference electrode formed in a region of said insulating substrate other than the region where said working electrode is formed;
a gas permeable membrane stretched over a portion of said insulating substrate to define an electrolyte chamber therebetween, said gas permeable membrane thereby covering said working electrode, said counter electrode and said reference electrode within the electrolyte chamber and having a peripheral portion supported on said insulating substrate;
an electrolytic solution in said electrolyte chamber defined between said gas permeable membrane and said insulating substrate;
wherein the peripheral portion of the gas permeable membrane is supported on said insulating substrate at a locus of support points, one said support point being displaced a minimum distance from said insulating substrate greater than or equal to the minimum such displacement of all other said support points, and wherein said working electrode has a surface that is displaced from said insulating substrate a distance greater than that of said one support point in the same direction as said one support point displacement, said direction being toward a non-peripheral portion of said stretched gas permeable membrane.

15. A planar oxygen sensor according to claim 14, wherein a portion of the insulating substrate surface inside the electrolyte chamber, other than the region where said working electrode is formed, is formed as a recessed bottom surface with respect to the portion of the insulating substrate on which said working electrode is formed.

16. A planar oxygen sensor according to claim 14, wherein said reference electrode serves to apply a constant voltage to said working electrode.

17. A planar oxygen sensor according to claim 14, wherein each of said working electrode and said counter electrode is formed of platinum.

18. A planar oxygen sensor according to claim 9, wherein said insulating substrate comprises a silicon dioxide film.

19. A planar oxygen sensor comprising:
an insulating substrate including a silicon substrate and a silicon dioxide film formed on said silicon substrate;
a frame formed so as to surround a part of said insulating substrate, said frame being formed of polyimide;
a working electrode formed on an upper surface of a support pad formed on said insulating substrate generally at the center of the part of the insulating substrate surrounded by said frame, said support pad being formed of polyimide;
a counter electrode and a reference electrode formed in a region of said insulating substrate inside said frame other than the region of said support pad;
a gas permeable membrane stretched over a portion of said insulating substrate to define an electrolyte chamber therebetween, said gas permeable membrane thereby covering said working electrode, said counter electrode and said reference electrode within the electrolyte chamber and having a peripheral portion fixed to and supported on said frame, said gas permeable membrane being formed of Teflon; and
an electrolytic gel in said electrolyte chamber defined between said gas permeable membrane, said frame and said insulating substrate;
wherein the peripheral portion of the gas permeable membrane is supported on said frame at a locus of support points, one said support point being displaced a minimum distance from said insulating substrate greater than or equal to the minimum such displacement of all other said support points, and wherein said working electrode has a surface that is displaced from said insulating substrate a distance greater than that of said one support point in the same direction as said one support point displacement, said direction being toward a non-peripheral portion of said stretched gas permeable membrane, the thickness of said silicon dioxide film being about 300 nm, the thickness of said support pad being about 50 $\mu$m, said working electrode and said counter electrode formed as a Ti—Pt two-layer film by photolithography, said reference electrode being formed as a Ti-Ag-AgCl three-layer film by photolithography, and the peripheral portion of said gas permeable membrane being bonded to said frame by an adhesive formed of an epoxy resin.

20. A planar oxygen sensor as claimed in claim 1, wherein the stretched gas permeable membrane and said cathode surface are separated only by a layer of said electrolytic solution.

21. A planar oxygen sensor as claimed in claim 1, wherein the stretched gas permeable membrane substantially contacts said cathode surface.

22. A planar oxygen sensor as claimed in claim 4, further comprising a silicon substrate supporting said silicon dioxide film.

23. A planar oxygen sensor as claimed in claim 5, wherein the stretched gas permeable membrane and said cathode surface are separated only by a layer of said electrolytic solution.

24. A planar oxygen sensor as claimed in claim 5, wherein the stretched gas permeable membrane substantially contacts said cathode surface.

25. A planar oxygen sensor as claimed in claim 8, further comprising a silicon substrate supporting said silicon dioxide film.

26. A planar oxygen sensor as claimed in claim 9, wherein the stretched gas permeable membrane and said working electrode surface are separated only by a layer of said electrolytic solution.

27. A planar oxygen sensor as claimed in claim 9, wherein the stretched gas permeable membrane substantially contacts said working electrode surface.

28. A planar oxygen sensor as claimed in claim 13, further comprising a silicon substrate supporting said silicon dioxide film.

29. A planar oxygen sensor as claimed in claim 14, wherein the stretched gas permeable membrane and said working electrode surface are separated only by a layer of said electrolytic solution.

30. A planar oxygen sensor as claimed in claim 14, wherein the stretched gas permeable membrane substantially contacts said working electrode surface.

31. A planar oxygen sensor as claimed in claim 18, further comprising a silicon substrate supporting said silicon dioxide film.

32. In a flow cell including a printed circuit board, a planar oxygen sensor supported by said printed circuit board, and a cap fixedly attached to said printed circuit board over said planar oxygen sensor, said cap including a flow passage for admitting a specimen to be tested to flow to said planar oxygen sensor, the improvement wherein said planar oxygen sensor comprises:
- an insulating substrate including a silicon substrate and a silicon dioxide film formed on said silicon substrate;
- a frame formed so as to surround a part of said insulating substrate, said frame being formed of polyimide;
- a working electrode formed on an upper surface of a support pad formed on said insulating substrate generally at the center of the part of the insulating substrate surrounded by said frame, said support pad being formed of polyimide;
- a counter electrode and a reference electrode formed in a region of said insulating substrate inside said frame other than the region of said support pad;
- a gas permeable membrane stretched over a portion of said insulating substrate to define an electrolyte chamber therebetween, said gas permeable membrane thereby covering said working electrode, said counter electrode and said reference electrode within the electrolyte chamber and having a peripheral portion fixed to and supported on said frame, said gas permeable membrane being formed of Teflon; and
- an electrolytic gel in said electrolyte chamber defined between said gas permeable membrane, said frame and said insulating substrate;
- wherein the peripheral portion of the gas permeable membrane is supported on said frame at a locus of support points, one said support point being displaced a minimum distance from said insulating substrate greater than or equal to the minimum such displacement of all other said support points, and wherein said working electrode has a surface that is displaced from said insulating substrate a distance greater than that of said one support point in the same direction as said one support point displacement, said direction being toward a non-peripheral portion of said stretched gas permeable membrane, the thickness of said silicon dioxide film being about 300 nm, the thickness of said support pad being about 50 $\mu$m, said working electrode and said counter electrode formed as a Ti-Pt two-layer film by photolithography, said reference electrode being formed as a Ti-Ag-AgCl three-layer film by photolithography, and the peripheral portion of said gas permeable membrane being bonded to said frame by an adhesive formed of an epoxy resin.

33. In a measuring system for measuring the oxygen content of a specimen flowing in a flow cell, the measuring system including a flow cell having a printed circuit board, a planar oxygen sensor supported by said printed circuit board, and a cap fixedly attached to said printed circuit board over said planar oxygen sensor, said cap including a flow passage for admitting a specimen to be tested to flow to said planar oxygen sensor; a first source of substantially pure oxygen gas; a second source of substantially pure nitrogen gas; first and second mixers each for mixing gas obtained from both the first and second sources, and for outputting respective first and second gas outputs of predetermined percentages; first and second gas bubblers each containing a buffer solution for dissolving said first and second gas outputs therein, respectively, and for outputting first and second specimens to said flow cell for measurement therein; the improvement wherein the planar oxygen sensor comprises:
- an insulting substrate including a silicon substrate and a silicon dioxide film formed on said silicon substrate;
- a frame formed so as to surround a part of said insulating substrate, said frame being formed of polyimide;
- a working electrode formed on an upper surface of a support pad formed on said insulating substrate generally at the center of the part of the insulating substrate surrounded by said frame, said support pad being formed of polyimide;
- a counter electrode and a reference electrode formed in a region of said insulating substrate inside said frame other than the region of said support pad;
- a gas permeable membrane stretched over a portion of said insulating substrate to define an electrolyte chamber therebetween, said gas permeable membrane thereby covering said working electrode, said counter electrode and said reference electrode within the electrolyte chamber and having a peripheral portion fixed to and supported on said frame, said gas permeable membrane being formed of Teflon; and
- an electrolytic gel in said electrolyte chamber defined between said gas permeable membrane, said frame and said insulating substrate;
- wherein the peripheral portion of the gas permeable membrane is supported on said frame at a locus of support points, one said support point being displaced a minimum distance from said insulating substrate greater than or equal to the minimum such displacement of all other said support points, and wherein said working electrode has a surface that is displaced from said insulating substrate a distance greater than that of said one support point in the same direction as said one support point displacement, said direction being toward a non-peripheral portion of said stretched gas permeable membrane, the thickness of said silicon dioxide film being about 300 nm, the thickness of said support pad being about 50 $\mu$m, said working electrode and said counter electrode formed as a Ti-Pt two-layer film by photolithography, said reference electrode being formed as a Ti-Ag-AgCl three-layer film by photolithography, and the peripheral portion of said gas permeable membrane being bonded to said frame by an adhesive formed of an epoxy resin.

* * * * *